United States Patent [19]
Shiber

[11] Patent Number: 4,979,939
[45] Date of Patent: * Dec. 25, 1990

[54] ATHERECTOMY SYSTEM WITH A GUIDE WIRE

[75] Inventor: Samuel Shiber, Billerica, Mass.

[73] Assignee: Surgical Systems & Instruments, Inc., Billerica, Mass.

[*] Notice: The portion of the term of this patent subsequent to Mar. 22, 2005 has been disclaimed.

[21] Appl. No.: 350,020

[22] Filed: May 12, 1989

Related U.S. Application Data

[63] Continuation-in-part of Ser. No. 326,967, Mar. 22, 1989, Pat. No. 4,957,482, Ser. No. 324,616, Mar. 16, 1989, Ser. No. 323,328, Mar. 13, 1989, and Ser. No. 322,497, Mar. 13, 1989, each is a continuation-in-part of Ser. No. 286,509, Dec. 19, 1988, Pat. No. 4,894,051, which is a continuation-in-part of Ser. No. 243,900, Sep. 13, 1988, Pat. No. 4,886,490, which is a continuation-in-part of Ser. No. 78,042, Jul. 27, 1987, Pat. No. 4,819,634, Ser. No. 205,479, Jun. 13, 1988, Pat. No. 4,883,458, and Ser. No. 225,880, Jul. 29, 1988, Pat. No. 4,842,579, each is a continuation-in-part of Ser. No. 18,083, Feb. 24, 1987, which is a continuation-in-part of Ser. No. 874,546, Jun. 16, 1986, Pat. No. 4,732,154, which is a continuation-in-part of Ser. No. 609,846, May 14, 1984, abandoned.

[51] Int. Cl.⁵ ............................................. A61B 17/32
[52] U.S. Cl. .................................... 606/159; 606/170; 604/22
[58] Field of Search ....................... 606/159, 170, 180; 604/22, 95, 264, 267

[56] References Cited

U.S. PATENT DOCUMENTS

| | | | |
|---|---|---|---|
| 4,669,469 | 6/1987 | Gifford, III et al. | 606/159 |
| 4,747,406 | 5/1988 | Nash | 604/22 X |
| 4,772,258 | 9/1988 | Marangoni et al. | 604/22 |
| 4,790,812 | 12/1988 | Hawkins, Jr. et al. | 604/22 |
| 4,886,490 | 12/1989 | Shiber | 604/22 |

Primary Examiner—Robert A. Hafer
Assistant Examiner—Kevin G. Rooney
Attorney, Agent, or Firm—Samuel Shiber

[57] ABSTRACT

An atherectomy system for coring, ingesting and removing an obstruction material from within a patient's vessel having a flexible guide-wire defining voids for containing obstruction material and defining a diametrical envelope, a flexible rotary-catheter slidable and rotatable over the diametrical envelope having a rotary coring means at its distal end, a continuous passage defined around the flexible guide-wire by the flexible rotary-catheter for ingesting the cored obstruction material, and coupling means at the proximal end of the flexible rotary-catheter for coupling to rotating means.

41 Claims, 7 Drawing Sheets

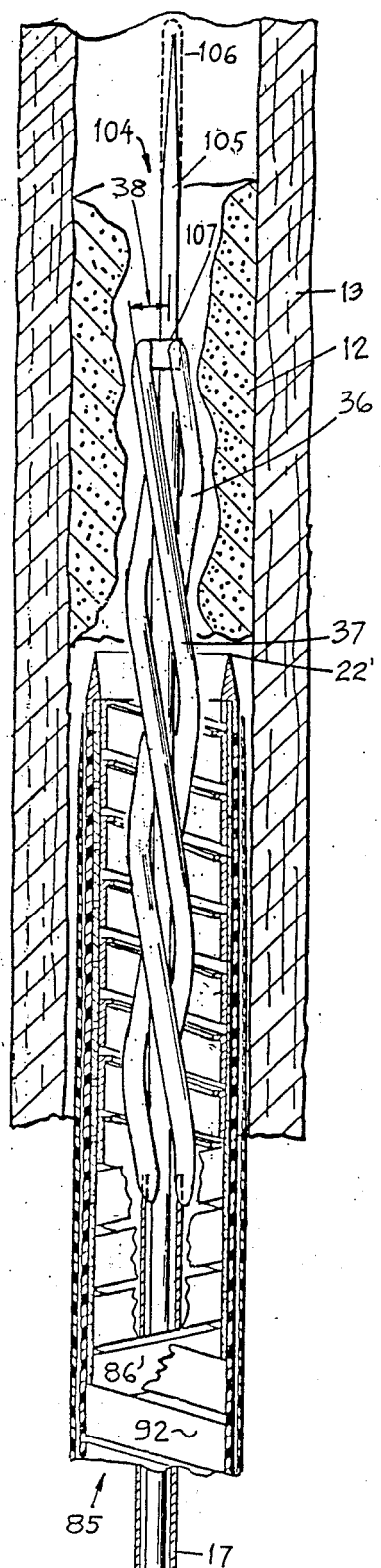
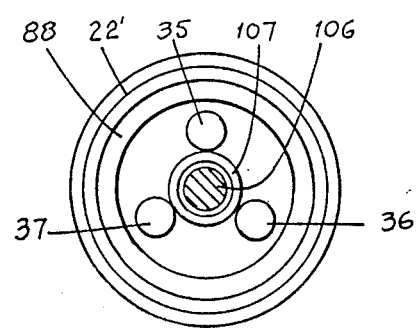
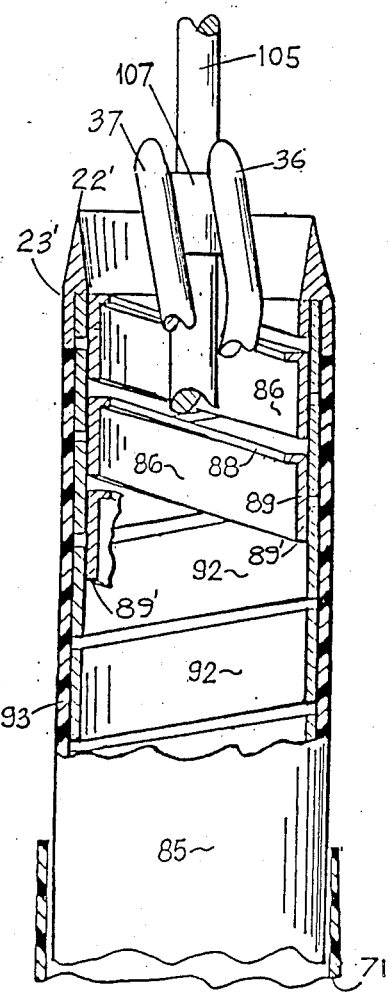
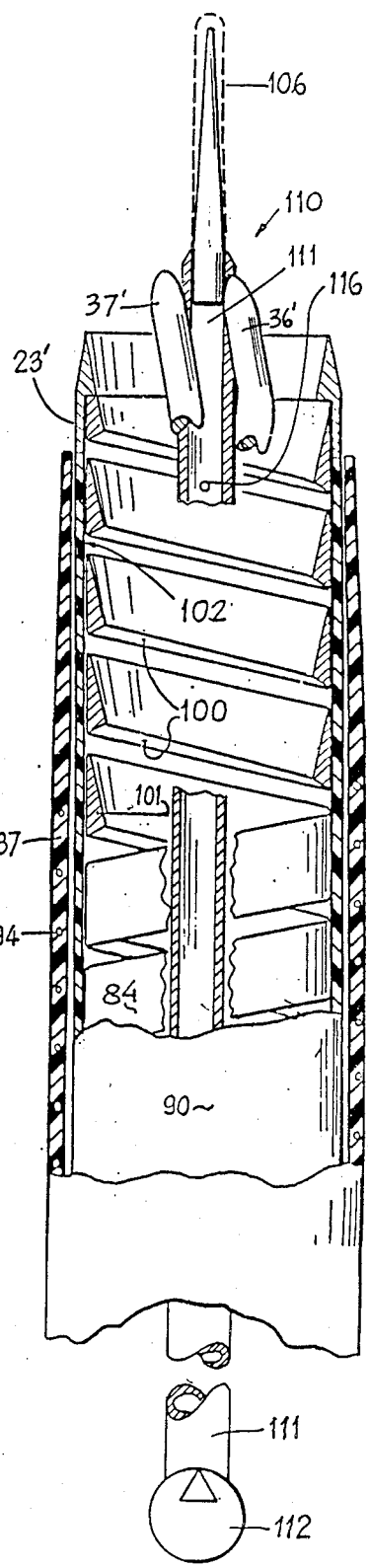
FIG. 4   FIG. 5   FIG. 6   FIG. 5'

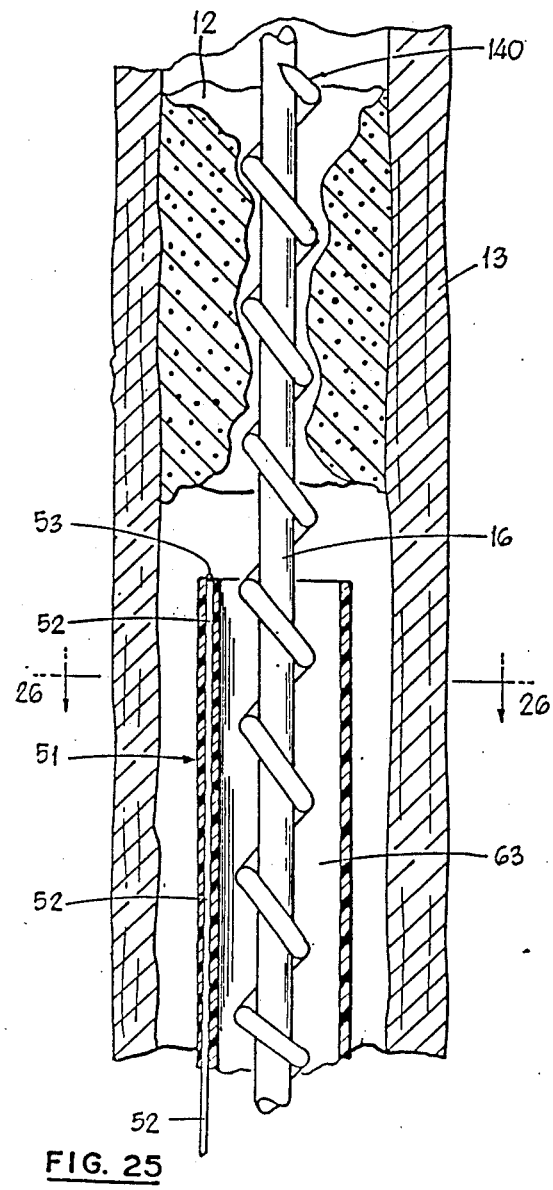
FIG. 25
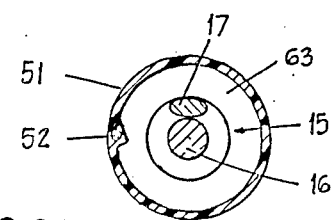
FIG. 26
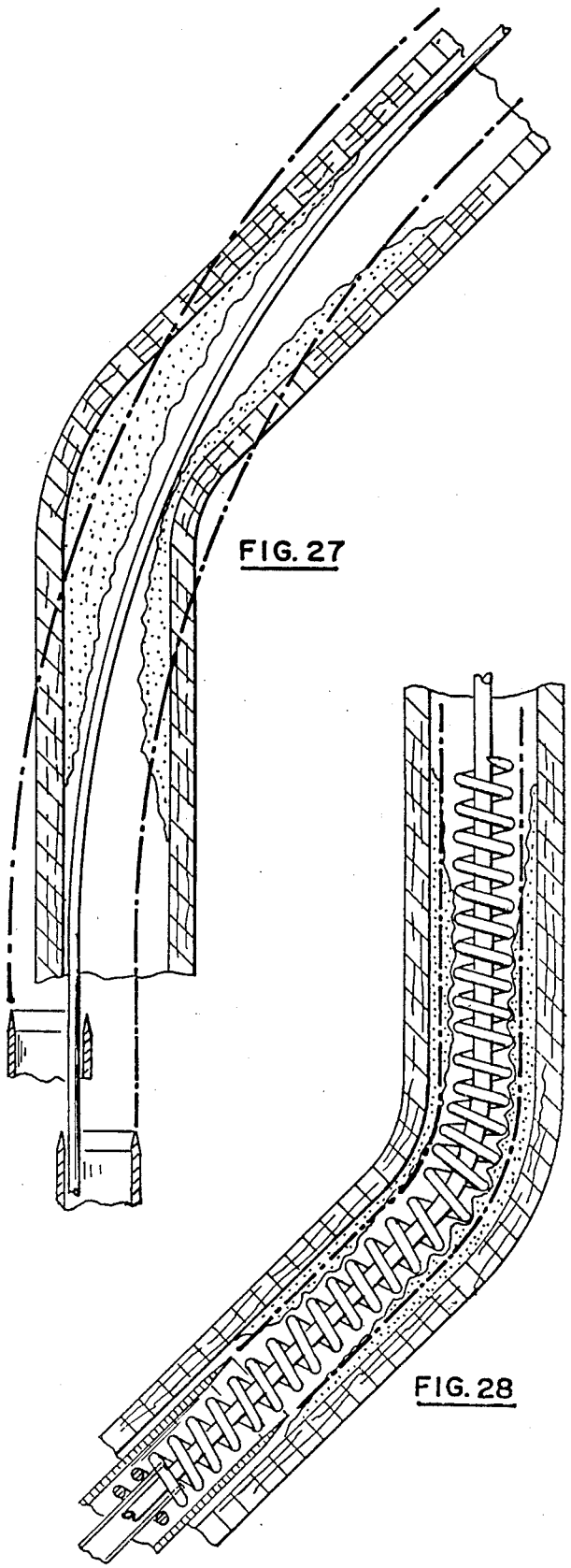
FIG. 27
FIG. 28

ATHERECTOMY SYSTEM WITH A GUIDE WIRE

CROSS REFERENCE TO OTHER APPLICATIONS AND BACKGROUND OF THE INVENTION

This application is a continuation in part (CIP) of four applications: application SN 07/326,967 filed on Mar. 22, 1989 (now U.S. Pat. No. 4,957,482), application SN 07/324,616 filed Mar. 16, 1989, application SN 07/323,328 filed Mar. 13, 1989, and application SN 07/322,497 filed Mar. 13, 1989. These four applications are CIP applications of application SN 07/286,509 filed Dec. 19, 1989 (now U.S. Pat. No. 4,894,051) which in a CIP of application SN 07/243,900 filed Sept. 13, 1988 (now U.S. Pat. No. 4,886,490), which is a CIP of three applications, application SN 07/078,042 filed Jul. 27, 1987 (now U.S. Pat. No. 4,819,634), application SN 07/205,479 filed Jun. 13, 1988 (now U.S. Pat. No. 4,883,458) and application SN 07/225,880 filed Jul. 29, 1988 (now U.S. Pat. 4,842,579). These three applications are CIPs of application SN 07/018,083 filed Feb. 24, 1987, which is a CIP of application SN 06/874,546 filed Jun. 16, 1968 (now Pat. No. 4,732,154) which is a CIP of application SN 06/609,846 filed May 14, 1984 (abandoned).

All the above applications are being incorporated herein by reference.

BACKGROUND AND OBJECTIVES OF THE INVENTION

With age a large percentage of the population develops atherosclerotic arterial obstructions resulting in diminished blood circulation. The disturbance to blood flow that these obstructions cause may induce blood clots which further diminish or block the blood flow. When this process occurs in the coronary arteries it is referred to as a heart attack. Presently such obstructions are circumvented by surgically grafting a bypass or they are treated by a catheter equipped with a balloon which is inserted through the arterial system, over a flexible guide-wire, into the obstruction and then inflated to expand the obstruction's lumen (angioplasty). Some of the problems with angioplasty are that it injures the arterial wall, it creates a rough lumen and in substantial number of the cases it is ineffective. Further, angioplasty does not remove the obstruction material out of the arterial system, therefore in a case of a heart attack, immediate angioplasty carries the risk of dislodging the blood clot and allowing it to move down stream creating additional blockages.

An objective of the present invention is to provide an atherectomy system having a flexible guide-wire with a diametrical envelope which rotatably and slidably supports a flexible catheter having a coring means at its distal end to core and extract the obstruction material, including blood clots if present, and create a smooth lumen without cracking the arterial wall. The flexible guide-wire defines voids for containing obstruction material. The design of an atherectomy catheter should lend itself to be producable in diameters down to approximately 1mm (millimeter) and a length of approximately a meter to enable it to reach and enter small and remote arteries. Preferably, the operation of the atherectomy system would resemble the operation of present catheter systems, so that existing skills of the medical staff can be utilized. These and other objectives of the invention will become apparent from the following discussion and the accompanying drawings.

BRIEF DESCRIPTION OF THE FIGURES

FIG. 2' shows a distal end of a flexible guide-wire having an elongated ultrasound transducer mounted at its distal tip. The transducer's distal end is equipped with teeth.

FIG. 4 shows a cross sectioned view of the distal end portion of an atherectomy system utilizing a flexible guide-wire having a casing made of triple windings. The flexible rotary-catheter is formed of an outer helical winding wound over an inner helical winding which includes a radially protruding helical step. A plastic jacket coats the outer winding.

FIG. 5 is an enlarged cross sectioned view of the distal end of the system shown in FIG. 4.

FIG. 5' shows a cross sectioned view of the distal end portion of an atherectomy system utilizing the flexible guide-wire having triple windings attached to a hollow core wire which serves to deliver contrast fluid to the vicinity of the proximal end of the flexible guide-wire. The flexible rotary-catheter is formed of a helical winding with a wire having a triangular cross section which provides a helical step for pushing the cored obstruction material proximally.

FIG. 6 shows a cross sectioned view of the distal end of the atherectomy systems shown in FIG. 5.

FIG. 25 shows a cross sectioned view of an atherectomy system where the rotary coring means utilizes a radiation emitting device.

FIG. 26 shows a cross sectioned view of the system shown in FIG. 25 along a line 26—26 marked on FIG. 25.

FIG. 27 shows cross sectioned view of a curved obstructed artery and the possible trajectory of the coring process when it is being done over a standard flexible guide-wire.

FIG. 28 shows cross sectioned view of a curved obstructed artery and the trajectory of the coring process when it is being done over a flexible guide-wire having a diametrical envelope over which the flexible rotary-catheter is slidably and rotatably supported.

DETAILED DESCRIPTION OF THE DRAWINGS

Figure 1:
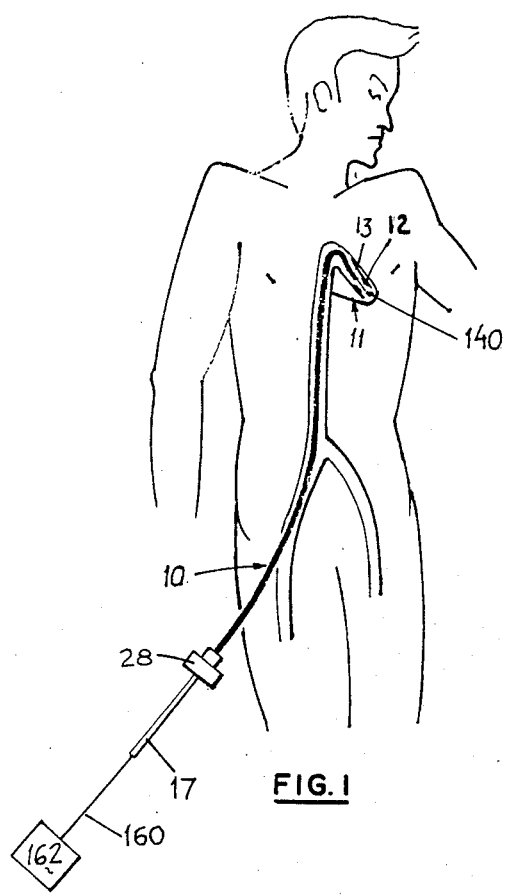
FIG. 1 generally shows an atherectomy system inserted at the groin area through the arterial system of a patient, into his obstructed coronary artery.

FIG. 1 generally shows an atherectomy system 10 inserted at the groin area, through a patient's arterial system into a coronary artery 13 serving the patient's heart 11.

Figure 2:
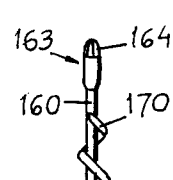
FIG. 2 shows a cross sectioned view of an atherectomy system with a flexible guide-wire having a flexible casing in the form of a helical wire and a flexible pilot-wire in the incorporating an ultrasound probe. The middle portion of the atherectomy system is removed due to space limitations on the drawing sheet.

FIG. 2 shows the atherectomy system 10 (similar parts will be indicated by same numbers throughout the FIGURES) for coring ingesting and removing an obstruction 12 from within a patient's vessel 13. The atherectomy system comprises several elongated parts in a nested relationship, and their ends shall be referred to as "distal" meaning the end which goes into the vessel and "proximal" meaning the other end. Thus, "distal direction" or "distally" shall indicate a general direction from the proximal end to the distal end, and "proximal direction" or "proximally" shall refer to an opposite direction.

The atherectomy system comprises:

A flexible guide-wire 140 insertable into the vessel.

A flexible rotary-catheter 21 slidable over the flexible guide-wire, having a rotary coring means in the form of a tubular-blade 22 at its distal end, defining a continuous passage 25 around the flexible guide-wire for ingesting the cored obstruction material.

The flexible guide-wire is made of a flexible pilot-wire in the form of a core wire 160 which is slidably and rotatably disposed in a helical wire 170 attached to a thin walled steel extension tube 17. The outer periphery of the helical wire forms a diametrical envelope over which the flexible rotary-catheter is rotatably and slidably supported and voids for containing the obstruction material are defined between the windings of the helical wire.

The diametrical envelope concentrically aligns the flexible rotary-catheter with the flexible guide-wire and the artery, the flexible guide-wire's section which extends distally from the flexible rotary-catheter into the artery provides a lever arm, which through the diametrical envelope, angularly aligns the flexible rotary-catheter with the flexible guide-wire and the artery.

The flexible rotary-catheter's distal end 23 slidingly and rotatably bears against the arterial wall spreading the contact force on a relatively large area and thereby minimizing the damage to the artery. A rotary coring means is efficient and uses less energy in comparison to other systems which pulverize the mass of the material of the obstruction. To illustrate this point, when a tubular-blade cores and extracts an obstruction with an outside diameter of 3 mm, an inside diameter (lumen) of 1 mm and a length of 10 mm the area that the tubular-blade has to cut through is 94.25 square mm. If a pulverizing blade, for example as shown in U.S. Pat. No. 4,445,509 by Auth, is used to break the same obstruction to particles measuring 0.01 mm by 0.01 mm by 0.01 mm the area that a pulverizing blade would have had to cut through is 37,699 square mm, and this area which is 400 times larger requires a much larger energy input to the blade, thereby substantially increasing the probability of traumatizing the artery.

Suction can be applied to the flexible rotary-catheter through a port 33 which communicates with a groove 34 defined by the motor's housing, which communicates with hole 39, which communicates with the hollow shaft which communicates with proximal end of the continuous passage 25. Preferably the suction is provided by a positive displacement pump 33' such as a piston pump or a peristalic pump which tends to self regulate the evacuation process, limiting the amount of blood removed through the flexible rotary-catheter to the volume that is positively displaced by the pump. When only free flowing blood is present in the continuous passage the negative pressure in the continuous passage drops. As obstruction material enters the continuous passage the negative pressure rises and pulls the cut material proximally (the level of negative pressure can be limited by a relief valve in the pump). The suction can be synchronized with the mechanical action or it can be otherwise selectively controlled, to further minimize blood evacuation. The suction cooperates with mechanical agitation and conveyance taking place in the continuous passage in moving the obstruction material proximally.

Coupling means at the proximal end of the flexible rotary-catheter in the form of a conical seat 27 couples it to rotating means in the form of a motor having a housing 28 and a hollow shaft 29 with a matching tapered end 31 and a seal 32 at its other end. The hollow shaft and seal are slidingly and rotatably disposed around the flexible guide-wire.

The core wire 160 contains means for transmission of ultrasound energy between an ultrasound transducer 161 mounted at its distal end and a base unit 162 connected to its proximal end. The base unit sends, through the core wire, low energy ultrasound waves to the transducer and receives back echo which is translated by the base unit to a visual map of the surrounding tissue. Relying on this information the physician can push the core wire forward without risking inadvertent perforation of the arterial wall. FIG. 2' shows a second embodiment of an ultrasound transducer 163 having teeth 164 on its distal end and a smooth proximal section for transmitting and receiving ultrasound waves. The teeth allow a physician to use the transducer as a drill by rotating the core wire in order to negotiate very tight obstructions or complete occlusions with the relative safety of knowing the transducer position relative to arterial wall. Alternatively, electromagnetic waves, such as laser energy, could be used with proper modification of the core wire 160 to carry electromagnetic waves, and of the transducer and base unit to transmit and receive such waves. With higher levels of energy sent from the base unit to the distal end of the flexible guide-wire, it is possible to assist the distal tip in penetrating through the obstruction or the occlusion.

FIG. 4, 5 and 6 show the distal end section of an atherectomy system with a flexible rotary-catheter 85 having an inner helical winding 86 with an inverted "L" cross section. The longer vertical part 89 forms a part of the inner-wall of the flexible rotary-catheter. Its bottom side 89' and a radially extending helical step 88 mechanically act on the cored material in the continuous passage pushing it proximally when the flexible rotary-catheter rotates forward ("forward rotation" of a part is defined herein as a clockwise rotation of the part when looking at its proximal end, "backward rotation" is an opposite rotation). The inner helical winding 86 tends to diametrically expand when the flexible rotary-catheter 85 is rotated forward by its proximal end, but this tendency is restrained by an outer helical winding 92, made of a flat thin ribbon and wound in a counter direction which tends to diametrically contract, acting as a hoop member balancing and restraining the inner winding's diametrical expansion.

A jacket 93 made of plastic with a low coefficient of friction coats and preferably is bonded to, the outer windings. A tubular blade 22' at the distal end of the windings provides a smooth outer surface 23' for slidingly bearing against an arterial wall while its sharp edge cores into an obstruction placed in front of it, and coupling means (not shown) is attached to the proximal end of the windings and has a conical seat for engaging the motor's shaft.

A flexible guide-wire 104 is made of a flexible pilot-wire 105 which is tapered at it distal end and covered with a fine spring to form a standard flexible tip 106, and, a casing in the form of a three wire windings 35, 36 and 37 which are attached, at their distal end to a common ring 107 and at their proximal end to an extension tube 17.

FIG. 5' shows an atherectomy system utilizing a flexible guide-wire 110 with triple wires 35' (not shown), 36' and 37' which are wound around and attached to a core wire in the form of a tube 111. Radio-opaque fluid, or other fluid, can be delivered by a pump 112 through the tube 111 and ejected through an orifice 116 at the distal end of the flexible guide-wire to facilitate fluroscopic imaging of the area. The flexible rotary-catheter 90 is formed of a helical winding 84 with a triangular wire cross section 101 which provides a protruding helical surface 100 to push the obstruction material proximally into the continuous passage as it rotates. The helical member is coated with a plastic layer forming a flexible tube 102. The flexible tube can extend distally to the blade. Alternatively the distal coils of the helical member 84 can be left bare to increase its flexibility and decrease its diameter or, the flexible tube 102 can be omitted all together. When the flexible tube is partially or completely missing the flexible rotary-catheter is not fluid worthy and in such cases a sleeve 87 can be distally extended to allow fluid conveyance and suction to reach the distal area of the atherectomy system. The sleeve 87 contains a helical reinforcement 94 to diametrically stabilize it as it is bent at the insertion point into the body (or into the artery in an intraoperative procedure) and elsewhere. Where the flexible tube is present it diametrically restrains the expansion of the helical member when torque is transmitted through it from the motor to the tubular blade.

The flexible guide-wire 140 shown in FIG. 2 does several things: It is a barrier countering distal movement of the obstruction material in the artery before and while it is being cored, it is an anti-rotational device which restrains the cored material from freely rotating around the flexible guide-wire and to the extent that the obstruction material does rotate around the flexible guide-wire this rotation is translated by the helix to urge the cored obstruction material proximally in the continuous passage. In addition when the flexible guide-wire has to be inserted into a tight obstruction the helix can be screwed into the obstruction by rotating it backwards.

Further, the helix guides the flexible rotary-catheter on the side of its wire 170, taking up the free play between the core wire ]6 and the flexible rotary-catheter If instead of a helix a conventional flexible guide-wire (with an outside diameter equal to the helix's outside diameter) was used, it would have made the system less effective and interfere with the insertion of the cored obstruction material into the continuous passage, as discussed above.

The helix can be modified by varying its helix angle and/or the number of wires coiled around its core wire. FIGS. 4, 5, and 6 show a flexible guide-wire with three wires 35, 36 and 37, attached to a ring 107 and surrounding the flexible pilot-wire 105. In case that the helix angle 38 is zero degrees, the wires 35, 36 and 37 are parallel to the core wire, and the flexible guide-wire is an anti-rotational device but is not effective by itself as a barrier or in urging the cored obstruction material into the continuous passage. These functions are increased as the angle 38 is increased. In an extreme case the helix angle can be made negative to decease the likelihood to the tubular-blade getting caught on the windings while following the flexible guide-wire along a curved section of an artery.

A flexible rotary-catheter that has means of pushing the cored obstruction material into the continuous passage, like the flexible rotary-catheter shown in FIGS. 4 or 5', may be teamed with flexible guide-wires which function mostly as anti-rotational or even the type mentioned above having a negative helix angle, whereas a flexible rotary-catheter without such additional means is preferably teamed with a flexible guide-wire having a positive helix angle.

Figure 8:
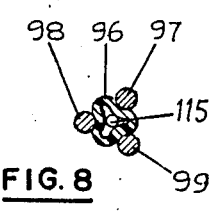
FIG. 8 shows a cross sectioned view of the relaxed flexible guide-wire shown in FIG. 7.
Figure 10:
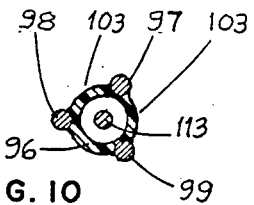
FIG. 10 shows a cross sectioned view of the expanded flexible guide-wire shown in FIG. 9.
Figure 7:
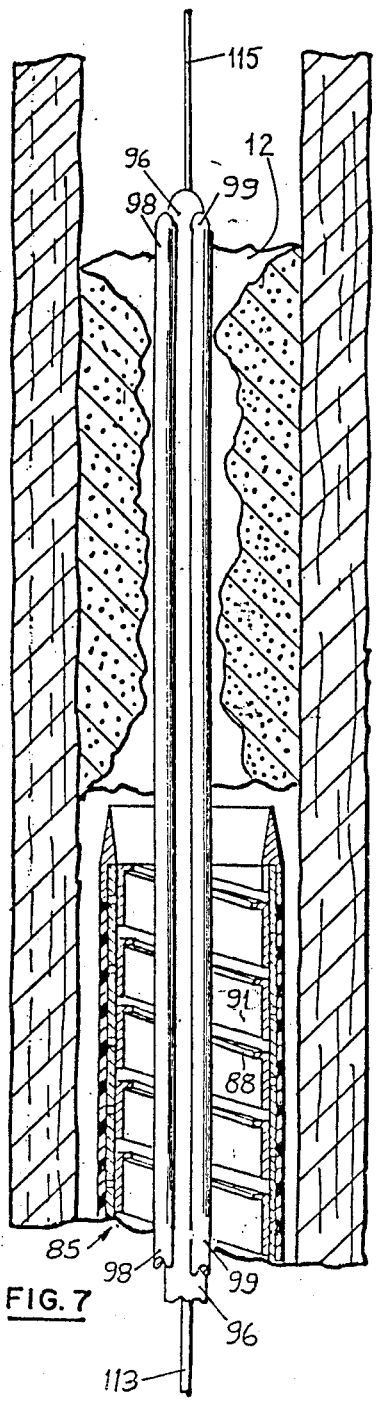
FIG. 7 shows a distal end portion of a flexible guide-wire having a hydraulically expandable casing (show: in its relaxed, contracted position) which is slidable over a flexible pilot-wire.
Figure 9:
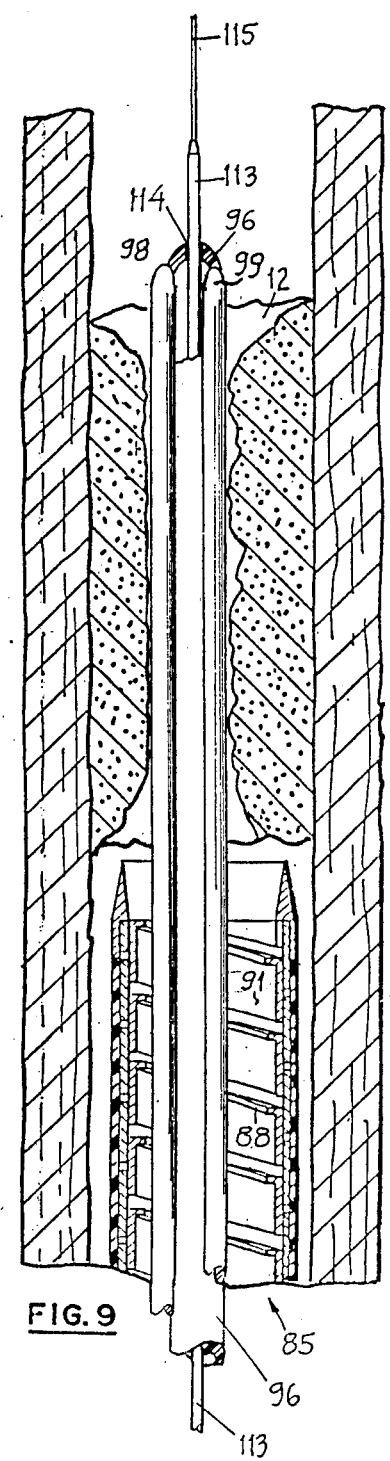
FIG. 9 shows a partially cross sectioned view of the flexible guide-wire shown in FIG. 7 shown in its energized, expanded position.

FIGS. 7 to 10 show a flexible guide-wire having a flexible pilot-wire 113 slidable in a casing in the form of a hydraulically expandable tube 96 carrying flexible wires 97, 98 and 99 forming longitudinal ridges thereon. In its relaxed position the tube has a clover leaf shape, harboring the elongated ridges as shown in FIGS. 7 and 8. The elongated tube is preferably made of a non streching material and can be selectively inflated and expanded with fluid to become round as shown in FIGS. 9 and 10, thereby radially displacing the elongated ridges outwardly, pushing them into the obstruction material and containing the material in the arced voids 103 between the ridges. One side of each wire, 97, 98, and 99, is bonded to the expandable tube and the opposite side defines a diametrical envelope over which the flexible rotary-catheter is rotatably supported. As the flexible rotary-catheter 85 is rotated and advance over the flexible guide-wire, it cores, ingests, and envelopes this obstruction's material. The helical step 88 utilizes the relative rotation to mechanically urge the obstruction material proximally into the continuous passage 91 while the ridges negate the material's rotation. When expanded the ridges move close to the helical step and provide positive guidance to the advancing flexible rotary-catheter. The flexible pilot-wire extends through a hole 114 defined by the distal end of the expandable tube. A distal section 115 of the flexible pilot-wire is reduced in diameter and when it is disposed in the hole, as shown in FIG. 7, it leaves a gap through which radio-opaque fluid or other fluid, introduced at the Proximal end of the expandable tube, can be delivered When the flexible pilot-wire is pushed distally, its full diameter section 113 seals the hole and the expandable tube can be effectively inflated, as shown in FIG. 9.

Figure 11:
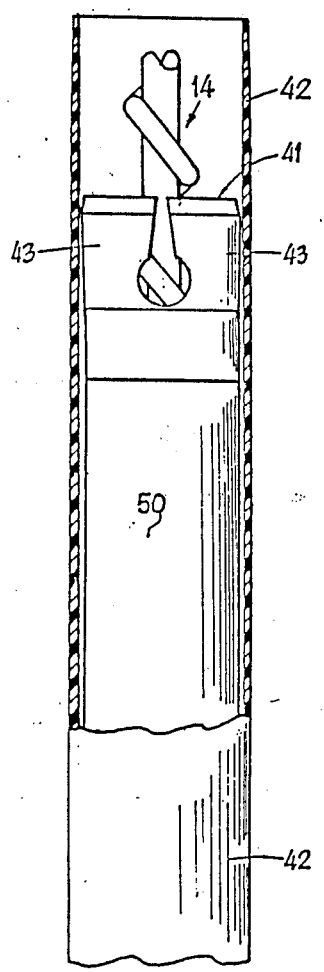
FIG. 11 shows the distal end portion of an atherectomy system having a rotary coring means in the form of a variable diameter tubular-blade, shown in its contracted position being compressed inside a sleeve.
Figure 13:
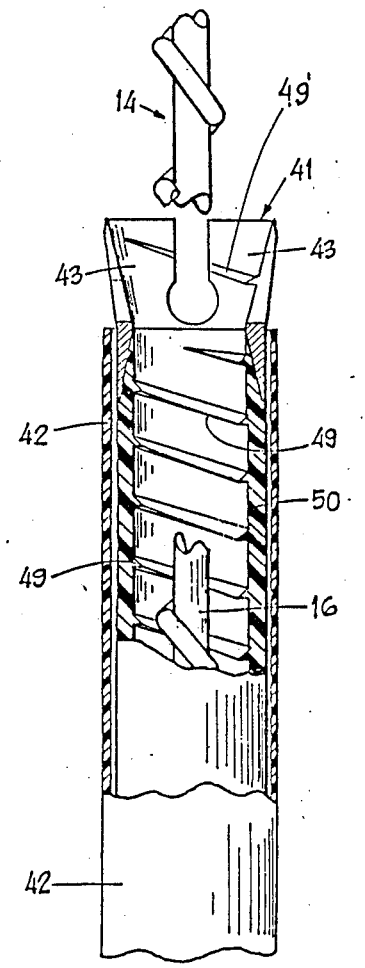
FIG. 13 shows a cross sectioned view of the variable diameter tubular-blade shown in FIG. 11 in its relaxed expanded position after it has emerged out of the sleeve. The variable diameter tubular-blade is mounted on a flexible rotary-catheter made of plastic with an integral helical step formed on its inner wall.
Figure 12:
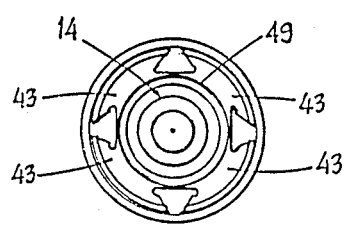
FIG. 12 shows the distal end of the variable diameter tubular-blade shown in FIG. 11.
Figure 14:
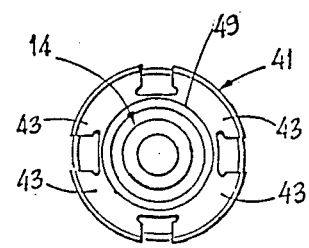
FIG. 14 shows the distal end of the variable diameter tubular-blade shown in FIG. 13.

FIGS. 11 and 12 show the rotary coring means being a variable diameter tubular-blade 41 in its contracted, compressed position as it is inserted into the vessel through a sleeve 42. The variable diameter tubular-blade (which superficially resembles a collet of the type used in mechanical pencils to grip the lead) is made of four flexible leaves 43 which move radially to their relaxed position, shown in FIGS. 13 and 14 when they exit and are no longer compressed by the sleeve. This reduces the size of the initial puncture wound needed to introduce a certain size rotary coring means into an artery and thereby reduces the associated bleeding and other healing problems of the puncture wound. FIG. 13 also illustrates a helical step 49 and 49' formed on the inner-wall of the flexible rotary-catheter 50 which pushes the cored obstruction material proximally. Step 49 is formed on the flexible rotary-catheter catheter portion of the inner wall and step 49' is formed on the tubular-blade's blade's portion of the inner wall.

Figure 15:
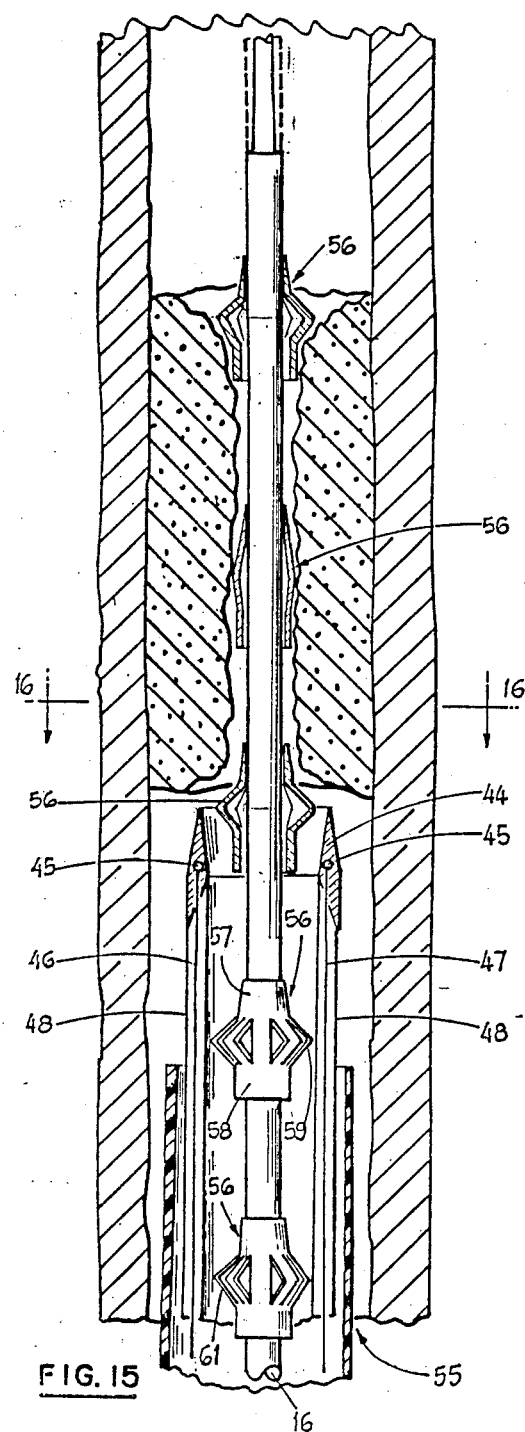
FIG. 15 shows a cross sectioned view of the distal end portion of an atherectomy system with a rotary coring means in the form of a heated tubular-blade, disposed over a flexible guide-wire having a pilot wire and a casing with barrier means.
Figure 16:
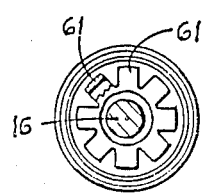
FIG. 16 shows a cross sectioned view of the system shown in FIG. 15 along a line 16—16 marked on FIG. 15.

FIG. 15 shows a distal end portion of an atherectomy system having a rotary coring means in the form of a heated tubular-blade 44 having a ring shaped heating element 45 embedded in the blade, to which energy is brought by means of two flexible conduits 46 and 47 embedded in a wall of a flexible rotary-catheter 48 (cross hatching of the catheter is omitted to show the conduits). The heating can be done electrically, in which case the conduits 46 and 47 are electrical wires and the heating element can be a resistive element, or the heating can be done with laser energy in which case the conduits 46 and 47 can be optical fibers and the heating element can serve to absorb the laser energy from the distal end of the optical fibers translating it to heat and distributing it to the tubular-blade 44. FIG. 15 further shows a flexible guide-wire which has a diametrical envelope in the form of barriers 56 to counter distal movement of surrounding obstruction material.

The barriers can be made of thin plastic tube sections They have a distal collar 57 affixed to the core wire 16 and a proximal collar 58 slidable on the core wire. These collars are connected to a slit collar 59. When the element 56 is Pushed through a tight obstruction, the slit collar can elastically deform and close to the configuration illustrated by the second from the top barrier element. Once past the obstruction the slit collar 59 springs back and bends its arms as illustrated by the top barrier element. In their open position the elements form a barrier to prevent the obstruction material from moving distally in the vessel and in the continuous passage while the flexible rotary-catheter cores and ingests the obstruction material The diameter of the streched out arms of the top barrier element can made larger than the inner diameter of the flexible rotary-catheter to block a larger cross sectional area of the artery whereas the diameter of the streched arms of the other barrier elements is made to fit inside the flexible rotary-catheter which they rotatably and slidably support.

Figure 17:
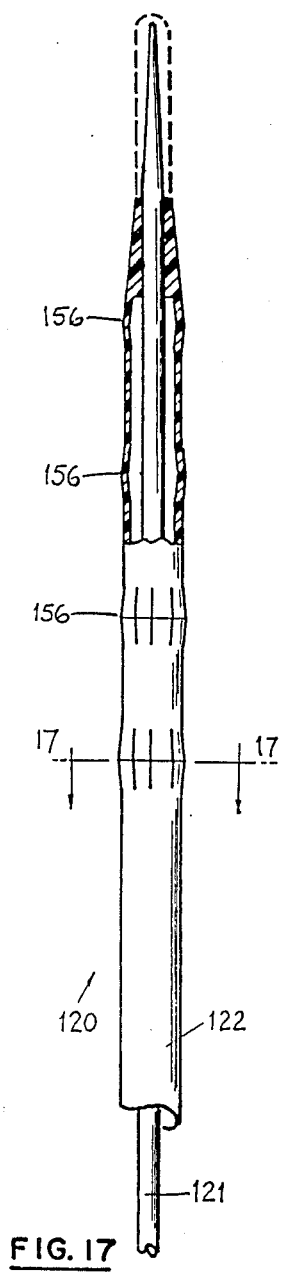
FIG. 17 shows a flexible guide-wire having a core wire and a casing in the form of a sleeve with selectively actuatable barrier means in their closed position.
Figure 18:
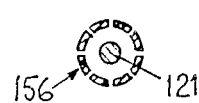
FIG. 18 shows a cross sectioned view of the flexible guide-wire shown in FIG. 17 along a line 18—18 marked on FIG. 17.
Figure 19:
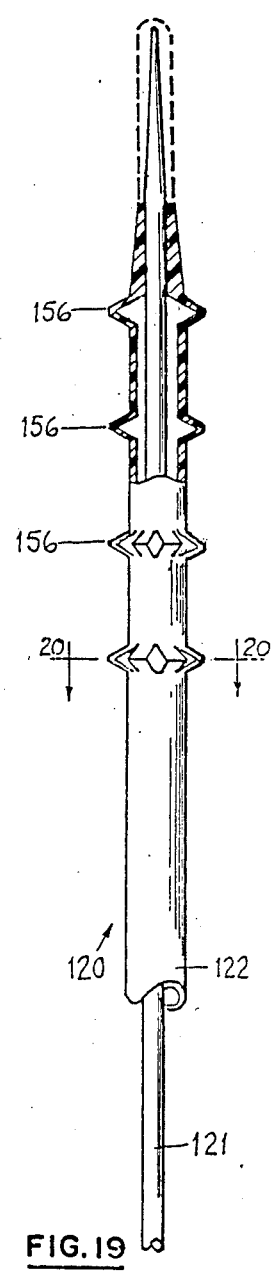
FIG. 19 shows the flexible guide-wire shown in FIG. 17 with the barrier means in their expanded position.
Figure 20:
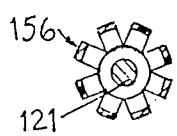
FIG. 20 shows a cross sectioned view of the flexible guide-wire shown in FIG. 19 along a line 20—20 marked on FIG. 19.

FIG. 17 to 20 show a flexible guide-wire 120 having a flexible core wire 121 and a thin walled tube 122 the distal end of which is bonded to the distal end of the flexible core-wire. Sets of short slits in the tube form barrier elements 156. The barrier elements are selectively expanded, as shown in FIGS. 19 and 20, and contracted, as shown in FIGS. 17 and 18, by pushing and pulling, respectively, the thin tube 60 relative to the core wire. When expanded, the barrier elements form a diametrical envelope over which the flexible rotary-catheter is slidably and rotatably supported and the voids between the barriers accept and hold the obstruction material during the atherectomy process.

Figure 21:
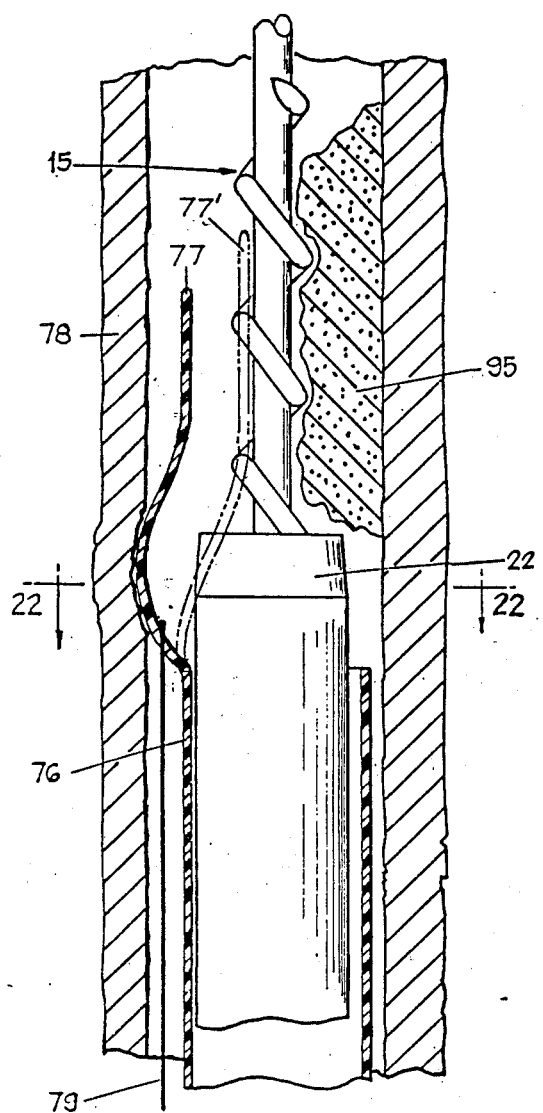
FIG. 21 shows a cross sectioned view of an atherectomy system with a flexible sleeve having a selectively actuatable tongue at its distal end.
Figure 22:
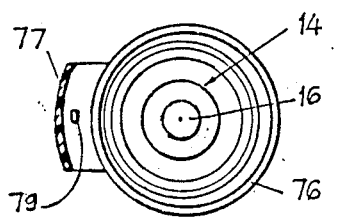
FIG. 22 shows a cross sectioned view of the tongue shown in FIG. 21 along the line 22—22 marked on FIG. 21.

FIGS. 21 and 22 show an atherectomy system where a flexible sleeve 76 has a tongue 77 which can be used when coring an eccentric obstruction 95. In such a case the tongue can be inserted opposite of the obstruction to protect an arterial wall 78 and bias the trajectory of the rotary coring means into the obstruction. The tongue can be energized against the arterial wall by tensioning a flexible rope 79, moving the tongue from its relaxed position shown in a phantom line in FIG. 21 and marked 77' to the position shown in solid lines and marked 77.

Figure 23:
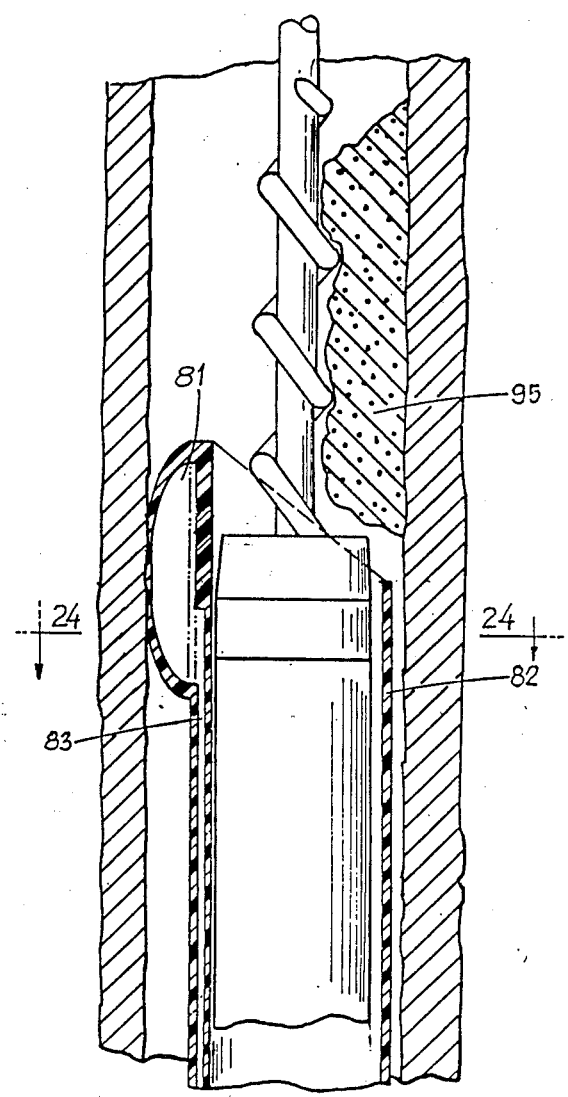
FIG. 23 shows a cross sectioned view of an inflatable chamber located at the distal end of the flexible sleeve.
Figure 24:
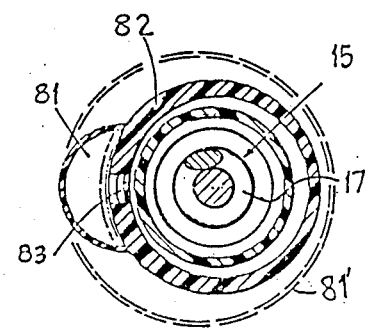
FIG. 24 shows a cross sectioned view of the chamber shown in FIG. 23 along a line 24—24 marked on FIG. 23.

FIG. 23 and 24 show an alternative biasing means in the form of an asymmetrical inflatable chambers 81 formed at the distal end of a flexible sleeve 82 which, when inflated, through a channel 83 formed in the sleeve's wall, hears against the vessel's wall, as shown in solid lines, eccentrically biasing the flexible sleeve and the rotary coring means. When deflated, as shown by phantom lines, the chamber conforms to the sleeve to minimize interference with its insertion into the vessel Alternatively the chamber can be shaped as an asymmetrical toroidal inflatable chamber 81' as shown in FIG. 24 by interrupted lines. This chamber, when inflated, establishes a peripheral contact with the arterial wall and thereby blocks blood flow between the sleeve and the arterial wall, as well as eccentricaly biasing the sleeve (it can be understood that a symmetrical toroidal chamber can be provided for the purpose of blocking the flow around the sleeve without eccentrically biasing the sleeve). Any of the above mentioned chambers can also be inserted into the lumen that has been cored by the rotary coring means, to be inflated therein, and to further widen the lumen, however, such a procedure may have some of the drawbacks of angioplasty.

FIGS. 25 and 26 show an atherectomy system having a flexible rotary-catheter 51 where the rotary coring means is a radiation emitting device such as optical fibers 52 which emits laser energy through a lens 53 aligned with the distal end of the fiber. The radiation energy cores the obstruction by cutting a narrow channel in it and the continuous passage 63 ingests the cored obstruction material as in previous embodiments. Similarly to the tubular-blade, the laser based rotary coring means is efficient and uses less energy in comparison to other laser based systems which pulverize the mass of the material of the obstruction. Using the same hypothetical obstruction which was used in the previous numerical example (having an outside diameter of 3 mm, an inside diameter of 1mm and a length of 10 mm) with the system shown in FIG. 25, when radiation energy is used to make a 0.1 mm wide peripheral cut, it has to disintegrate 9.11 cubic mm of material which is 14.5% of the obstruction's volume. The flexible rotary-catheter 51 can be rotatably disposed in any of the sleeves shown in connection to the previous embodiments. By using a sleeve equipped with a toroidal chamber to block blood flow as explained above and by introducing fluid, saline solution for example, through the sleeve or the flexible rotary-catheter, a working medium of choice can be created to suite a specific type of radiation and to allow visual or spectroscopic analysis of the arterial lumen. Alternative forms of radiation energy such as ultrasound can also be used in which case the optical bundle will be replaced by a suitable medium for carrying ultrasound energy.

Figure 3:
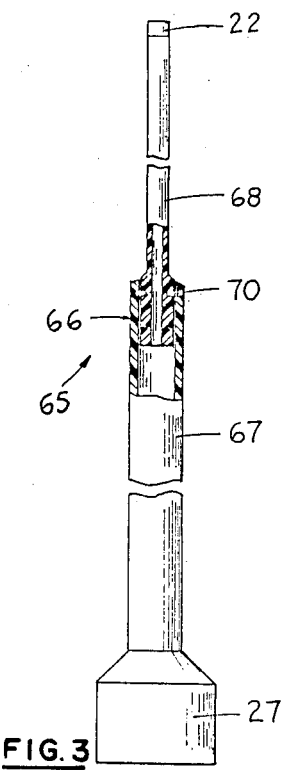
FIG. 3 shows a cross sectioned view of a flexible rotary-catheter equipped with a torque limiting clutch between its proximal end portion and distal end portion.
Figure 2:
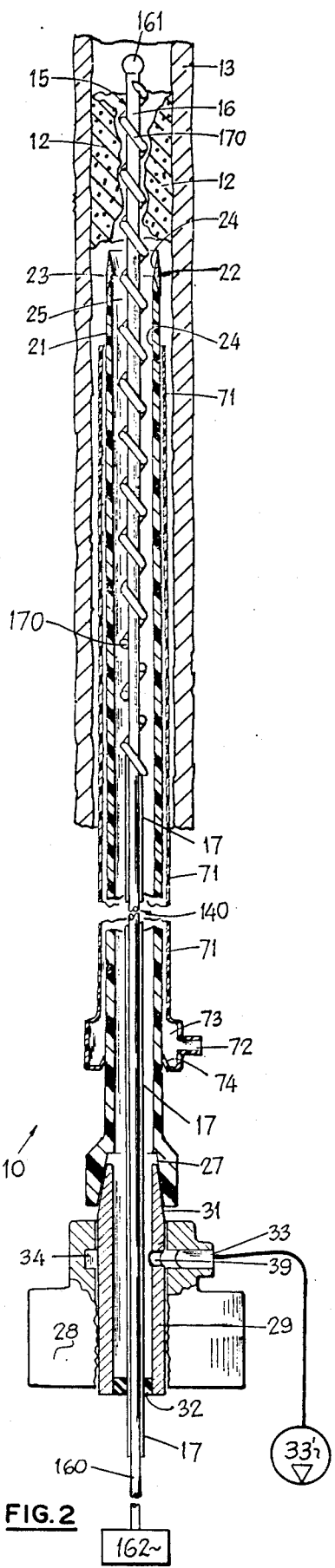

Torque generated by the motor is partially dissipated by frictional losses along the flexible rotary-catheter, therefore, the flexible rotary-catheter can be manufactured with a variable cross section, for example, an increased outside diameter and or/wall thickness at the vicinity of its proximal end compared with the same at its distal end, as shown in FIGS. 2 and 3. This gives the flexible rotary-catheter an increased stiffness and torque carrying capacity in the vicinity of its proximal end. Such a design is useful when treating small arteries in the heart or brain while entering the arterial system at the groin area as shown in FIG. 1, which requires a long pushable flexible rotary-catheter having a flexible distal end portion as small as 1 mm. As shown in FIG. 3 the flexible rotary-catheter 65 can be equipped with a torque limiting clutch 66 between the proximal and distal sections, 67 and 68, respectively, of the flexible rotary-catheter. The clutch is made by press fitting the section 68 into section 67 to establish frictional engagement between the two which limits the torque capacity of the clutch 66 to a certain permissible value, thereby protecting the smaller distal end from damage by occasional transfer of higher torques that may be applied at the proximal end. A lock-ring 70 prevents relative longitudinal displacement between sections 67 and 68 while not interfering with their relative rotation.

Referring back to FIG. 2, a flexible sleeve 71 in which the flexible rotary-catheter is rotatably disposed protects the arterial wall from the rotating catheter and can be used to introduce the flexible rotary-catheter into the vessel. Means for introducing fluids into the vessel are connected to the flexible sleeve in the form of a nipple 72 leading into an annular chamber 73 which communicates with the sleeve. The annular chamber is equipped with a seal 74 which seals around the flexible rotary-catheter and forces fluid entering the nipple 72 to continue and move distallY in the sleeve around the flexible rotary-catheter.

FIG. 27 illustrates the possibility of injuring the arterial wall when the flexible rotary-catheter is working over, and is loosely guided by, a standard flexible guide-wire. As the tubular blade advances along the flexible guide-wire it can move sideways any where between the two extreme positions shown at the bottom of the FIGURE, relative to the flexible guide-wire. Therefore, any material disposed between the phantom lines may be cored by the flexible rotary-catheter, including large segments of the arterial wall. The phantom lines marked on FIG. 28 illustrate the improved trajectory of the rotary coring means when it is guided over a diametrical envelope which closely guides the flexible rotary-catheter within the artery while removing more of the obstruction material and avoiding the arterial wall.

The atherectomy system can be manufactured in different diameters and lengths depending on the size and site of artery that it is intended for and on whether the system is to he used percutaneously (that is through the skin) or intra-operatively (that is when the vessel is surgically exposed for inserting the system into the vessel). It can be noted from the FIGURES that the basic components of the atherectomy system can accept several optional features: The flexible rotary-catheter can be made from plastic or metal and either version can be equipped with a helical step. The rotary coring means can vary. The flexible guide-wire can be equipped with anti-rotational means, a barrier or a helix. The sleeve can be equipped with mechanical or hydraulic biasing and flow blocking means. By combining a flexible rotary-catheter with certain features, a flexible guide-wire with certain features and a sleeve with a certain added features a variety of species can be made. This increases the user's ability to match the system's characteristics with the specific condition that is treated, which is helpful, since the clinical characteristics of arterial atherosclerotic obstructions vary in geometry, hardness, and accessibility.

OPERATION

A process for removing an obstruction from a vessel with an atherectomy system, comprises the following steps:

1. Inserting into a vessel, into an obstruction, a flexible pilot wire. The flexible pilot-wire can be constructed like a standard flexible guide-wire, or it can be equipped with various means to assist the physician in guiding it through the arterial system and the obstruction, such as, ultrasound or light imaging of the arterial environment surrounding the distal end of the flexible guide-wire, or by providing a conduit for delivering radio-opaque fluid to the flexible guide-wire distal end to facilitate fluoroscopic imaging of the process.

2. Inserting into a vessel, into an obstruction, over the flexible Pilot-wire a flexible casing having a diametrical envelope which defines voids for containing the obstruction material. The distal portion the flexible pilot wire which has been inserted in the vessel bears along several centimeters of the vessel wall and provides a lever arm to angularly align the advancing casing with the flexible pilot-wire and the artery (in a case where a "one piece" flexible guide-wire like the one shown in FIG. 5', insertion of the flexible guide-wire into the vessel is done as a single step which replaces the above two steps).

3. Advancing and rotating, over the diametrical envelope, a rotary coring means located at a distal end of a flexible atherectomy catheter, coring and ingesting the obstruction material. During the coring the rotary coring means is rotatably supported within the artery by the flexible guide-wire through the diametrical envelope. Concentric and angular alignment is provided by the flexible guide-wire through its diametrical envelope to the advancing rotary coring means and to the flexible rotary-catheter and the distal portion of the flexible guide-wire which extends distally, ahead of the rotary coring means, and bears against the artery for a length of several centimeters provides a lever arm to angularly align the advancing rotary coring means and the flexible guide-wire with the artery. Without the benefit of this alignment the flexible rotary-catheter is likely to contact the arterial wall at a steeper angle and require a higher force to bend it to conform top the arterial curvature, increasing the risk of arterial perforation.

4. Removing the atherectomy system containing the obstruction material out of the vessel.

Suction, which is preferably provided by a positive displacement pump means, may be used to assist the mechanical action in enabling the cored obstruction material to move proximally in the continuous passage.

The sequence of insertion of the components into the artery may vary depending on the nature and the location of the obstruction and the preferences of the medical staff. Additional steps may be added to assist the process. A standard guiding catheter, which is either straight or pre-formed, may function as a sleeve and be inserted into the vessel to assist in placing the flexible guide-wire and the atherectomy catheter in the obstruction site.

While the present invention has been illustrated by a limited number of embodiments, it should be understood that various modifications and substitutions may be made without departing from the spirit of the invention or the scope of the claims.

I claim:

1. An atherectomy system for coring, ingesting and removing an obstruction material from within a patient's vessel, comprising in combination:
   a flexible guide-wire insertable into the vessel,
   a flexible rotary-catheter slidable over said flexible guide-wire, having a rotary coring means at its distal end,
   a continuous passage defined around said flexible guide-wire by said flexible rotary-catheter for ingesting the cored obstruction material,
   coupling means at a proximal end of said flexible rotary-catheter for coupling to rotating means,
   said flexible guide-wire having a diametrical envelope over which said flexible rotary-catheter is rotatably and slidably supported, said envelope defining voids for containing the obstruction material.

2. An atherectomy system as in claim 1, wherein said diametrical envelope concentrically aligns the flexible rotary-catheter with the flexible guide-wire and the artery.

3. An atherectomy system as in claim 1, said flexible guide-wire's portion which is inserted into said vessel distally to said flexible rotary-catheter provides a lever arm to angularly align said flexible rotary-catheter with the flexible guide-wire and the artery.

4. An atherectomy system as in claim 1, wherein said flexible guide-wire comprises a flexible pilot wire and a flexible casing slidable thereon.

5. An atherectomy system as in claim 4, a portion of said flexible pilot wire which is inserted in said vessel distally to said casing provides a lever arm to angularly align said casing with the flexible pilot-wire and the artery.

6. An atherectomy system as in claim 1, wherein said diametrical envelope comprises at least one radially protruding elongated ridge.

7. An atherectomy system as in claim 6, wherein said elongated ridge is a helix.

8. An atherectomy system as in claim 6, wherein said protrusion of said elongated radially protruding ridge is selectively controlled.

9. An atherectomy system as in claim 8, wherein said envelope comprise an expandable tube with at least one elongated ridge on its periphery.

10. An atherectomy system as in claim 1, said rotary coring means being a tubular-blade.

11. An atherectomy system as in claim 1, said rotary coring means being a variable diameter tubular-blade.

12. An atherectomy system as in claim 1, said rotary coring means being a heated tubular-blade.

13. An atherectomy system as in claim 1, said rotary coring means being a radiation emitting device.

14. An atherectomy system as in claim 1, said diametrical envelope comprises a radially protruding barrier means.

15. An atherectomy system as in claim 14, wherein said barrier means can elastically contract to pass through a narrowed lumen.

16. An atherectomy system as in claim 14, wherein said barrier means can be selectively contracted to pass through a narrowed lumen.

17. An atherectomy system as in claim 1, wherein said flexible rotary-catheter is stiffer and has a higher torque carrying capacity in the vicinity of said proximal end than in the vicinity of said distal end.

18. An atherectomy system as in claim 1, having a flexible sleeve in which said flexible rotary-catheter is rotatably disposed.

19. An atherectomy system as in claim 18, said flexible sleeve having a biasing means for eccentrically biasing said flexible sleeve in the vessel.

20. An atherectomy system as in claim 19, said biasing means comprise a selectively inflatable asymmetrical chamber formed at said distal end of said flexible sleeve.

21. An atherectomy system as in claim 19, said flexible sleeve having a tongue at its distal end for eccentrically biasing said flexible sleeve in the vessel.

22. An atherectomy system as in claim 21, said tongue being selectively actuatable.

23. An atherectomy system as in claim 18, wherein means for introducing fluids into the vessel are connected to said flexible sleeve.

24. An atherectomy system as in claim 1, wherein said flexible rotary-catheter comprises a helical member which pushes the cored obstruction material proximally while said flexible rotary-catheter rotates around said flexible guide-wire.

25. An atherectomy system as in claim 1, wherein suction is applied at said Proximal end of said continuous passage to proximally pull the cored obstruction material in said continuous passage.

26. An atherectomy system as in claim 25, wherein said suction is formed by a positive displacement pump means.

27. An atherectomy system as in claim 1, wherein said flexible guide-wire comprises a tube for transmitting fluid from its proximal end to its distal end.

28. An atherectomy system as in claim 1, wherein said flexible guide-wire is equipped with an ultrasound transducer at its distal end and is connected to a base unit at its proximal end, said flexible guide-wire containing means for transmission of ultrasound energy between said transducer and said base unit.

29. An atherectomy system as in claim 1, wherein said flexible guide-wire is equipped with an laser transducer at its distal end and is connected to a base unit at its proximal end, said flexible guide-wire containing means for transmission of laser energy between said transducer and said base unit.

30. A process for removing an obstruction from an vessel with an atherectomy system, comprising the following steps:
   inserting into a vessel, into an obstruction, a flexible guide-wire, having a diametrical envelope which contains voids for accepting the obstruction material,
   advancing over the flexible guide-wire a rotary coring means located at a distal end of an atherectomy catheter,
   advancing and rotating the rotary coring means into the obstruction and coring the obstruction while the rotary coring means is rotatably supported and aligned with the artery by the diametrical envelope,
   removing the atherectomy system containing the obstruction material out of the vessel.

31. A process as in claim 30, wherein said flexible guide-wire is inserted into the vessel under ultrasound guidance.

32. A process as in claim 30, wherein said flexible guide-wire is inserted into the vessel under visual guidance 33. A process as in claim 30, wherein a radio-opaque fluid is injected through the distal end of said flexible guide-wire as it is inserted into the vessel under fluoroscopic guidance.

34. A process as in claim 30, wherein suction is used to assist the mechanical action in enabling the cored obstruction material to move proximally in the continuous passage.

35. A process as in claim 34, wherein said suction is provided by a positive displacement pump means.

36. A process for removing an obstruction from a vessel with an atherectomy system, comprising the following steps:
   inserting into a vessel, into an obstruction, a flexible pilot wire,
   inserting into a vessel, into an obstruction, over the flexible pilot-wire a flexible casing having a diametrical envelope which contains voids for accepting the obstruction material,
   advancing over the casing a rotary coring means located at a distal end of an atherectomy catheter,
   advancing and rotating the rotary coring means into the obstruction and coring the obstruction while the rotary coring means is rotatably supported and aligned with the artery by the diametrical envelope,
   removing the atherectomy system containing the obstruction material out of the vessel.

37. A process as in claim 36, wherein said flexible guide-wire is inserted into the vessel under ultrasound guidance.

38. A process as in claim 36, wherein said flexible guide-wire is inserted into the vessel under visual guidance.

39. A process as in claim 36, wherein a radio-opaque fluid is injected through the distal end of said flexible guide-wire as it is inserted into the vessel under fluoroscopic guidance.

40. A process as in claim 36, wherein suction is used to assist the mechanical action in enabling the cored obstruction material to move Proximally in the continuous passage.

41. A process as in claim 40, wherein said suction is provided by a positive displacement pump means.

* * * * *